US010222351B2

(12) United States Patent
Kondoh

(10) Patent No.: US 10,222,351 B2
(45) Date of Patent: Mar. 5, 2019

(54) WIRE ROPE INSPECTION APPARATUS

(71) Applicant: TOKYO ROPE MANUFACTURING CO., LTD., Tokyo (JP)

(72) Inventor: Johsei Kondoh, Tokyo (JP)

(73) Assignee: TOKYO ROPE MANUFACTURING CO., LTD., Tokyo (JP)

(*) Notice: Subject to any disclaimer, the term of this patent is extended or adjusted under 35 U.S.C. 154(b) by 238 days.

(21) Appl. No.: 15/298,120

(22) Filed: Oct. 19, 2016

(65) Prior Publication Data

US 2017/0038338 A1 Feb. 9, 2017

Related U.S. Application Data

(63) Continuation of application No. PCT/JP2014/061873, filed on Apr. 28, 2014.

(51) Int. Cl.
| | |
|---|---|
| *G01N 27/82* | (2006.01) |
| *G01N 27/83* | (2006.01) |
| *F16G 11/00* | (2006.01) |
| *F16G 11/10* | (2006.01) |
| *B66B 7/12* | (2006.01) |
| *B66B 5/00* | (2006.01) |

(52) U.S. Cl.
CPC ............ *G01N 27/83* (2013.01); *G01N 27/82* (2013.01)

(58) Field of Classification Search
CPC . Y10T 24/3936; Y10T 24/39; Y10T 24/3956; Y10T 24/1418; Y10T 24/3947; B66B 7/123; B66B 7/1215; B66B 7/1223; F16G 11/101; F16G 11/14
See application file for complete search history.

(56) References Cited

U.S. PATENT DOCUMENTS

| | | | | | |
|---|---|---|---|---|---|
| 4,145,920 | A | * | 3/1979 | Yamagami | B66B 7/1223 187/266 |
| 4,427,940 | A | * | 1/1984 | Hirama | B66B 7/123 324/206 |
| 4,475,843 | A | * | 10/1984 | Wyler | E04C 5/166 256/55 |
| 4,493,134 | A | * | 1/1985 | Karr | F16G 11/14 174/92 |

(Continued)

FOREIGN PATENT DOCUMENTS

| | | |
|---|---|---|
| CN | 2205557 Y | 8/1995 |
| CN | 102713597 A | 10/2012 |

(Continued)

OTHER PUBLICATIONS

International Search Report (ISR) (PCT Form PCT/ISA/210), in PCT/JP2014/061873, dated Jun. 3, 2014.

(Continued)

*Primary Examiner* — Alesa Allgood
(74) *Attorney, Agent, or Firm* — McGinn IP Law Group, PLLC.

(57) ABSTRACT

Provided is a wire rope inspection apparatus that is light, small in size and portable. A portable rope tester has a sensor device for sensing magnetic leakage flux leaking from a magnetized wire rope. Provided on the front of sensor device is a sensor face formed to be flat. The sensor face is pressed against the wire rope. By pressing the flat sensor face against the wire rope, magnetic leakage flux is sensed by the sensor device and whether the wire rope is damaged or not is detected. A handle is secured to the back of the sensor device on the side opposite the sensor face. The sensor device is held by grasping the handle by hand, and the sensor face of the device is pressed against the wire rope.

6 Claims, 14 Drawing Sheets

(56) References Cited

U.S. PATENT DOCUMENTS

| | | | | |
|---|---|---|---|---|
| 4,594,752 | A * | 6/1986 | Garner, Sr. | F16G 11/101 24/132 R |
| 4,827,215 | A * | 5/1989 | van der Walt | G01N 27/82 324/227 |
| 5,068,949 | A * | 12/1991 | Horace | F16G 11/101 24/115 R |
| 6,633,159 | B1 * | 10/2003 | Robar | B66B 7/1223 324/240 |
| 7,123,030 | B2 * | 10/2006 | Robar | B66B 7/1223 324/693 |
| 8,476,898 | B2 * | 7/2013 | Nishiyori | B66B 7/123 187/393 |
| 9,470,657 | B2 * | 10/2016 | Ouellette | G01R 33/04 |
| 2010/0259253 | A1 * | 10/2010 | Nishiyori | B66B 7/123 324/240 |

FOREIGN PATENT DOCUMENTS

| | | |
|---|---|---|
| EP | 1 186 565 A2 | 3/2002 |
| JP | S 62-1165 U | 1/1987 |
| JP | H 01-49898 B2 | 10/1989 |
| JP | H 02-32248 A | 2/1990 |
| JP | H 04-203962 A | 7/1992 |
| JP | H 04-114711 U | 10/1992 |
| JP | H 05-18939 A | 1/1993 |
| JP | 2001-063938 A | 3/2001 |
| JP | 2002-181792 A | 6/2002 |
| JP | 2006-071603 A | 3/2006 |
| JP | 2010-210272 A | 9/2010 |
| WO | WO 2011/148456 A1 | 12/2011 |
| WO | WO 2012-169008 A1 | 12/2012 |
| WO | WO 2014-016978 A1 | 1/2014 |

OTHER PUBLICATIONS

PCT/IPEA/409 in PCT/JP2014/061873, dated Jul. 8, 2016.

Chinese Office Action, dated Dec. 5, 2018, in Chinese Application No. 201480078431.8 and English Translation thereof.

* cited by examiner

WIRE ROPE INSPECTION APPARATUS

CROSS-REFERENCE TO RELATED APPLICATION

This application is a Continuation of PCT International Application No. PCT/JP2014/061873 filed on Apr. 28, 2014. The above application is hereby expressly incorporated by reference, in its entirety, into the present application.

BACKGROUND OF THE INVENTION

Field of the Invention

The present invention relates to a wire rope inspection apparatus.

Description of the Related Art

Known in the art is an inspection apparatus which uses magnetic leakage flux to inspect for damage to a wire rope for elevators and cranes (Patent Documents 1 and 2).

A wire rope flaw detection apparatus described in Patent Document 1 is equipped with a sensor unit having a shape that surrounds the major portion of the outer peripheral surface of a wire rope. Since the area of contact between the wire rope and the sensor unit is large, wear sustained by the wire rope and sensor unit, which is produced owing to contact between the wire rope and sensor unit, proceeds at a rapid pace. Wear is hastened even further if the sensor unit is installed permanently in fixed fashion. Further, the sensor unit has a size conforming to the diameter of the wire rope. Since the sensor unit must be designed in conformity with the diameter of the wire rope inspected, the apparatus lacks versatility.

Patent Document 2 describes a rope flaw detection apparatus for subjecting multiple wire ropes to flaw inspection simultaneously. A plurality of abnormality detectors inclusive of magnetic sensors are provided in association with respective ones of the multiple wire ropes. Since the abnormality detector in Patent Document 2 also surrounds the major portion of the outer peripheral surface of the wire rope, wear sustained by the wire rope and sensor unit proceeds at a rapid pace. Furthermore, since an abnormality detector is provided for each one of multiple wire ropes according to Patent Document 2, the overall apparatus is heavy and large in size. Further, since it is necessary to design the rope flaw detection apparatus in accordance with the spacing between the wire ropes, the apparatus lacks versatility.

PRIOR ART DOCUMENTS

Patent Document 1: International Patent Application Laid-Open No. WO2011/148456
Patent Document 2: Japanese Patent Application Laid-Open No. 2006-71603

SUMMARY OF THE INVENTION

An object of the present invention is to provide a light-weight, small-size, portable wire rope inspection apparatus.

Another object of the present invention is to provide a wire rope inspection apparatus in which a wire rope and sensor device sustain little wear.

A further object of the present invention is to arrange it so that a common sensor device can be used irrespective of the diameter of the wire rope inspected and number of wire ropes inspected.

A wire rope inspection apparatus according to a first aspect of the present invention has a sensor device for sensing magnetic leakage flux that leaks from a magnetized wire rope, characterized in that the sensor device has a flat sensor face pressed against the wire rope, and has a handle secured to a portion of a face of the sensor device other than the sensor face thereof.

A magnetic flux flows into a magnetized wire rope. If damage exists in the wire rope, the magnetic flux will leak into space (to the outside) in the region of the damage. By sensing the magnetic flux (leakage flux), which leaks into space, using a sensor device, the existence of damage to the wire rope can be detected. In order to sense leakage flux (a change in the magnetic flux), the magnetized wire rope may be moved and the sensor device held fixed or, conversely, the sensor device may be moved and the magnetized wire rope held fixed. In either case, the wire rope inspection apparatus according to this aspect of the present invention inspects a wire rope by sensing magnetic leakage flux from the magnetized wire rope.

According to the first aspect of the present invention, the sensor face of the sensor device that senses magnetic leakage flux from a magnetized wire rope is flat (planar). The flat sensor face is pressed against the wire rope. Since a wire rope has a cross section that is approximately circular, the sensor face comes into line contact with the wire rope when magnetic leakage flux is sensed. The area of contact between the sensor face and the wire rope is small and the sensor face and wire rope undergo little wear.

Further, since the sensor device employs a flat sensor face, it is unnecessary to prepare sensor devices of different shapes and sizes in accordance with the diameter of the wire rope inspected, and a common sensor device can be used. Further, by simultaneously pressing the flat sensor face of the sensor device against multiple wire ropes arrayed in parallel, multiple wire ropes can be inspected collectively. Even if the number of wire ropes and the spacing between multiple wire ropes differ, a common sensor device can be used. Furthermore, since multiple wire ropes can be inspected collectively using a single sensor device and not employing multiple sensor devices corresponding to respective one of the multiple wire ropes, an inspection apparatus that is light in weight and small in size is realized.

When a wire rope is inspected, the flat sensor face of the sensor device is pressed against the wire rope, as mentioned above. Since a handle is secured to a portion of a face of the sensor device other than the sensor face thereof, the sensor device can be held by grasping the handle, the sensor face of the device can be faced toward the wire rope and brought close to it and can be pressed against the wire rope. The handle may be a single handle (in a case where the sensor device is held by one hand) or two handles may be provided (in a case where the sensor device is held by both hands). Since the inspection apparatus according to this aspect of the present invention is thus transportable (portable), the inspection apparatus is brought to the site where the wire rope has been installed and is suited to on-site inspection of the wire rope that has been installed (that is in use). Since the sensor face of the sensor device is pressed against the wire rope only when the wire rope is inspected, wear sustained by the sensor device and wire rope is much less in comparison with an inspection apparatus permanently installed in fixed fashion.

Preferably, the above-mentioned sensor device has a sensing coil for sensing magnetic leakage flux, and a magnetizer for magnetizing the wire rope. Both magnetization of the wire rope and sensing of magnetic leakage flux can be performed using a single sensor device. Preferably, magnetization of the wire rope by the magnetizer is stopped at unsaturated magnetization, which is magnetization that does not attain saturation.

In an embodiment, the sensor device includes two, first and second, of the sensing coils, these being arranged in parallel, spaced-apart relation and differentially connected, wherein spacing between portions of respective ones of the first and second sensing coils through which the magnetic leakage flux passes is an integral multiple of distance between adjacent strands of multiple strands that constitute the wire rope. In a case where a wire rope is formed by twisting multiple strands together, magnetic leakage flux will leak from unevenness among multiple strands. By constructing the sensing coil from the first and second sensing coils differentially connected and arranged in parallel, spaced-part relation, and making the spacing between the portions of respective ones of the first and second sensing coils through which the magnetic leakage flux passes an integral multiple of the distance between the adjacent strands of multiple strands that constitute the wire rope, a signal that arises from the magnetic leakage flux arising from the unevenness between the strands can be substantially cancelled. The portion of a waveform (strand noise) which is ascribable to the unevenness between strands, and which appears in the waveform of the test signal, can be suppressed.

A wire rope inspection apparatus according to a second aspect of the present invention has a sensor device for sensing magnetic leakage flux that leaks from a magnetized wire rope, wherein the sensor device has a flat sensor face pressed against the wire rope, and a tilting mechanism is attached to a back side of the sensor device. The tilting mechanism includes: multiple connecting shafts provided projectingly on a back face of the sensor device on the side opposite the sensor face; a bracket formed to have through-holes through which respective ones of the multiple connecting shafts pass, the bracket being attached to the back side of the sensor device by the connecting shafts that have been passed through the through-holes; a fixing member fixed to a distal end portion of each of the connecting shafts passed through the through-holes; and biasing part (means) provided between the sensor device and the bracket for biasing the sensor device and the bracket away from each other. Compression coil springs through which respective ones of the multiple connecting shafts are passed can be used as the biasing part (means). The above-mentioned handle can be secured to the bracket directly or indirectly.

In the second aspect of the present invention as well, the flat sensor face of the sensor device is pressed against the wire rope when the wire rope is inspected. The area of contact between the sensor face of wire rope is small and, hence, wear sustained by the sensor face and wire rope is small. Further, with regard to wire ropes the diameters of which differ, use can be made of a common sensor device, and a common sensor device can be used even if the number of wire ropes inspected differs.

According to the second aspect of the present invention, the sensor device and the bracket are biased away from each other by the biasing part (means). Since the fixing member is fixed to a distal end portion of each of the connecting shafts passed through the through-holes formed in the bracket, the biased bracket comes into contact with the fixing members and will not fall off the connecting shafts. In a state in which a force is not acting in a direction that causes the sensor device and bracket to approach each other, a gap forms between the sensor device and bracket. The connecting shafts are passed through the through-holes, which are formed in the bracket, and are not fixed to the bracket. When a force acts that pushes the sensor device in a direction extending from its front (sensor face) toward its back, therefore, the biasing part is compressed and the sensor device and bracket approach each other. The sensor device can also assume an attitude in which it is tilted with respect to the bracket. When the sensor face of the sensor device is pressed against a wire rope, it is possible for the sensor device to tilt, as mentioned above, even if the sensor face is pressed against the wire rope obliquely. The wire rope, therefore, is easily brought into line contact with the sensor face. This improves the accuracy with which magnetic leakage flux is sensed, namely the accuracy of detection of wire rope damage.

Preferably, the tilting mechanism has a tilt regulating screw screwed into the bracket movably back and forth near each of the multiple connecting shafts with the distal end of the screw being directed toward the back face of the sensor device. By turning the tilt regulating screws, the amount of protrusion of the tilt regulating screws from the bracket is adjusted. If the amount of protrusion of a tilt regulating screw from the bracket is enlarged, the back face of the sensor device will contact the distal end of the tilt regulating screw when the sensor device tilts. The inclination of the sensor device, therefore, can be stopped at this point (no further tilting is allowed). The angle through which the sensor device is capable of tilting can be adjusted.

A wire rope inspection apparatus according to a third aspect of the present invention has a sensor device for sensing magnetic leakage flux that leaks from a magnetized wire rope, wherein the sensor device has a flat sensor face pressed against the wire rope, the apparatus including a pair of guide members removably attached to both side portions of the sensor device and having a prescribed thickness extending outwardly from the sensor face of the sensor device. In the third aspect of the present invention as well, the sensor face is flat and, hence, the sensor face and wire rope sustain little wear. Further, a common sensor device can be used with regard to wire ropes the diameters of which differ, and a common sensor device can be used even if the number of wire ropes inspected differs.

According to the third aspect of the present invention, a pair of guide members having a prescribed thickness extending outwardly from the flat sensor face are removably attached to both side portions of the sensor device. Since the wire rope inspected can be sandwiched from both its sides by the pair of guide members, movement of the wire rope in the width direction [the lateral direction when the sensor device is viewed from its front (sensor face) and the direction orthogonal to the longitudinal direction of the wire rope] is limited. A stable test signal can be acquired.

A wire rope inspection apparatus according to a fourth aspect of the present invention has a sensor device for sensing magnetic leakage flux that leaks from a magnetized wire rope, wherein two, first and second, sensor devices are provided, both of the first and second sensor devices having a flat sensor face pressed against the wire rope. By making use of two sensor devices, the sensor faces of the two sensor devices can be pressed against respective ones of both sides (both faces) of the wire rope, not just one side (one face) of the wire rope, and magnetic leakage flux can be sensed on both sides of the wire rope. This improves the accuracy with which magnetic leakage flux is sensed, namely the accuracy of detection of wire rope damage.

Preferably, the wire rope inspection apparatus according to the fourth aspect of the present invention is such that the first sensor device has a sensing coil for sensing magnetic leakage flux, and a magnetizer for magnetizing the wire rope, and the second sensor device has a sensing coil for sensing magnetic leakage flux but does not have a magnetizer for magnetizing the wire rope. By bringing the two sensor faces into opposition across the wire rope, the wire rope sandwiched by the first sensor device and second sensor device can be magnetized by the magnetizer with which the first sensor device is equipped. This makes it possible to provide the second sensor device with only the sensing coil and not a magnetizer. It is possible to achieve a reduction in the weight of the inspection apparatus that includes the first and second sensor devices, and it becomes easier to carry the inspection apparatus.

Preferably, a positioning fitting having a pin-insertion hole is outwardly projectingly provided on both side faces of each of the first and second sensor devices, and the apparatus has connecting pins that are passed through the pin-insertion holes for connecting the positioning fittings of the first sensor device to the positioning fittings of the second sensor device. The sensor faces of the first and second sensor devices can be made to face each other squarely across the wire rope.

In an embodiment, the wire rope inspection apparatus has test signal accepting device (means) for accepting a test signal that is output from the sensor device; and a control unit (signal processor and warning generator) for generating at least one of light or sound when a test signal having a value equal to or greater than a predetermined value is accepted by the test signal accepting device. A warning to the effect that a wire rope is damaged can be issued to a worker at the site where the wire rope has been installed.

DESCRIPTION OF THE PREFERRED EMBODIMENTS

Figure 1:
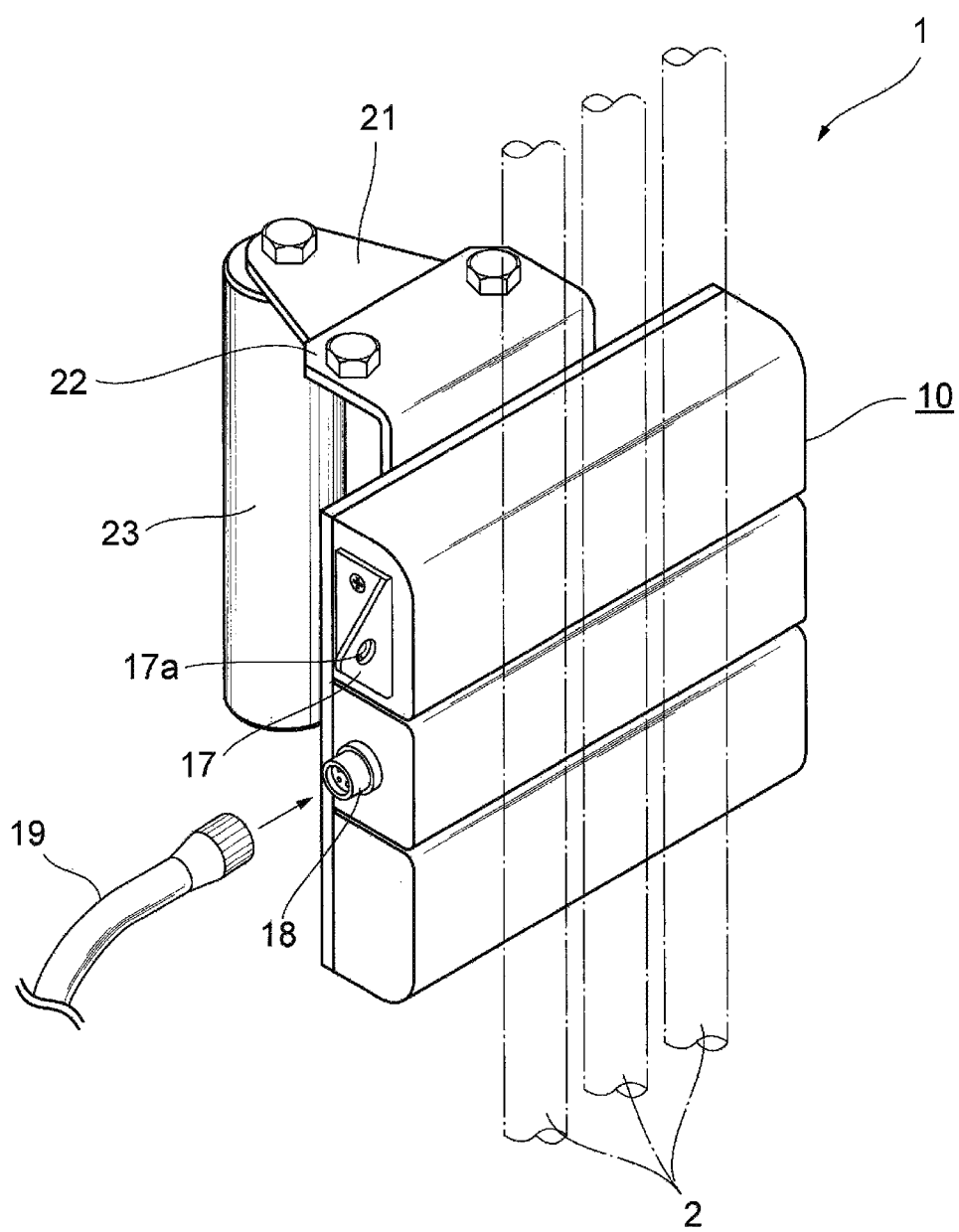
FIG. 1 is a perspective view of a portable rope tester.
Figure 2:
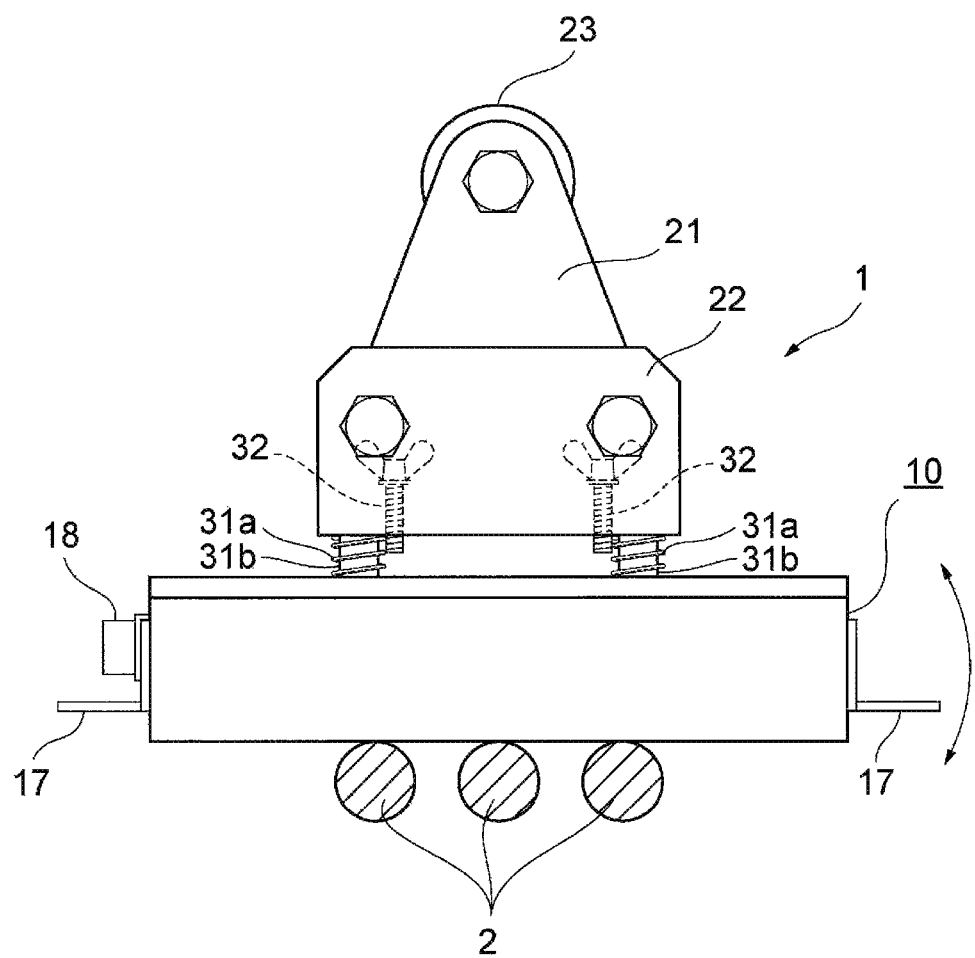
FIG. 2 is a plan view of a portable rope tester.
Figure 3:
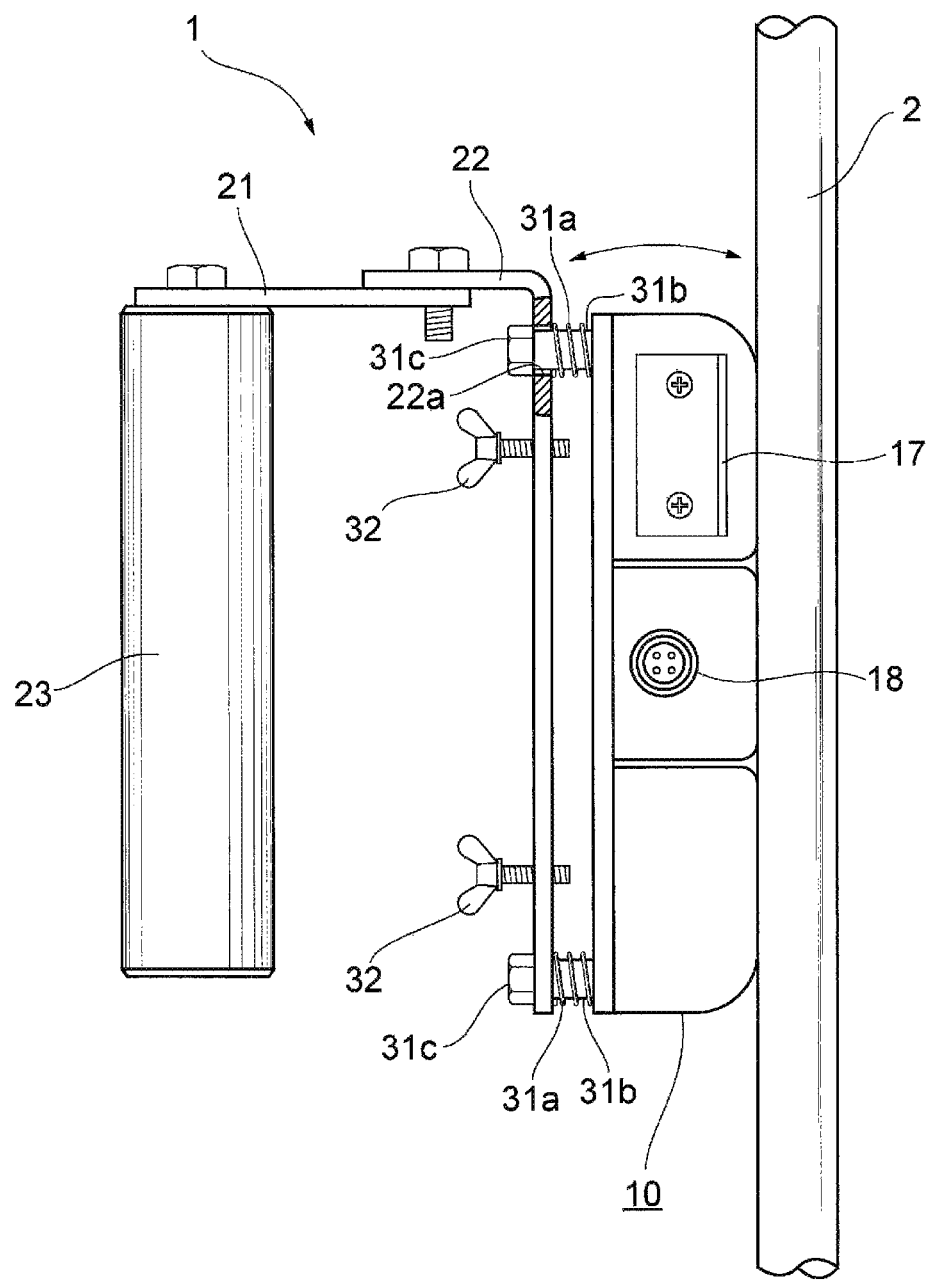
FIG. 3 is a side view of a portable rope tester.

FIG. 1 is a perspective view when a portable rope tester is viewed from the front, FIG. 2 is a plan view of the portable rope tester, and FIG. 3 is a side view of the portable rope tester.

A portable rope tester 1, which is used to inspect a wire rope 2 and, more particularly, to detect damage (inclusive of severance) of the wire rope 2, has a sensor device 10, brackets 21, 22 provided on the back side of the sensor device 10, and a handle 23. The portable rope tester 1 is comparatively light and is portable.

Although the details will be described later, the sensor device 10 has a sensing coil. Electromotive force, which is generated in the sensing coil due to a change in magnetic flux from the wire rope 2 passing through the sensing coil, is used to determine whether the wire rope 2 has sustained damage. It is necessary, therefore, to move either the sensor device 10 (rope tester 1) or the wire rope 2. If the wire rope 2 inspected is a wire rope used in an elevator, for example, the wire rope 2 will moved by operating the elevator and the sensor device 10 (rope tester 1), therefore, can be kept at rest. It is also possible to inspect a wire rope 2 that is at rest. In this case, the wire rope 2 is inspected by moving the sensor device 10 (rope tester 1) along the wire rope 2.

The overall shape of the sensor device 10 is a rectangular parallelepiped and is substantially square when viewed from the front. Its length (width) in the lateral direction when viewed from the front may be greater than its length in the vertical direction, i.e., lateral width may be increased. When the wire rope 2 is inspected, the front of the sensor device 10 is pressed against the wire rope 2 upon arranging it so that the longitudinal direction of the wire rope 2 and the width direction (lateral direction) of the sensor device 10 intersect, preferably orthogonally. In order to press the front of the sensor device 10 against the wire rope 2, the columnar handle 23 is attached to the back side of the sensor device 10 via the brackets 21, 22. The rope tester 1 can be held in one hand by grasping the handle 23. It may be arranged so that two handles 23 are attached to, for example, the bracket 22 in spaced-part relation so that the rope tester 1 can be held with two hands.

The front of the sensor device 10 that will be pressed against the wire rope 2 is substantially flat. The flat front of the sensor device 10 pressed against the wire rope 2 shall be called the "sensor face". FIGS. 1 to 3 illustrate the manner in which three wire ropes 2 extending in parallel in spaced-part relation are inspected collectively. Since each wire rope 2 has a cross section that is substantially circular, each of the three wire ropes 2 comes into line contact with the sensor face of the sensor device 10. Wire ropes 2 inspected may be one or two or four or more. In case of inspection of multiple wire ropes 2 disposed in such number that they exceed the length of the sensor device 10 in the width direction thereof, it is possible to inspect the multiple wire ropes 2 collectively using a plurality of the portable rope testers 1. A plurality of the portable rope testers 1 may be arrayed on a straight line along the width direction or may be arrayed along the width direction with the positions thereof staggered along the vertical direction.

The back face (rear face) of the sensor device 10 on the side opposite the sensor face also is formed flat. With reference to FIGS. 2 and 3, four bolts (connecting shafts) 31b have been secured to the back face of the sensor device 10 spaced apart from one another at locations corresponding to four corners of a rectangle. The four bolts 31b projecting to the rear pass through respective ones of compression springs 31a and the bracket 22 is attached to the four bolts. Formed in the bracket 22 are four through-holes 22a (only one through-hole 22a is illustrated in FIG. 3) through which respective ones of the four bolts 31b are passed. A nut 31c is fixed to the distal end of each bolt 31b passing through the through-hole 22a formed in the bracket 22.

Each bolt 31b connecting the sensor device 10 and bracket 22 is passed through the respective compression coil spring 31a, as mentioned above, and the spring is sandwiched between the sensor device 10 and bracket 22. The sensor device 10 and bracket 22 are biased away from each other by the compression coil spring 31a and, as a consequence, a gap is formed between the sensor device 10 and bracket 22. As mentioned above, the bolt 31b is passed through the through-hole 22a formed in the bracket 22 and the bolt 31b and bracket 22 are not fixed to each other. When a force acts that pushes the sensor device 10 along a direction extending from the front to the back thereof, the compression coil spring 31a is compressed, the bolt 31b protrudes to the rear from the bracket 22 and the sensor device 10 and bracket 22 approach each other. When the force pushing the sensor device 10 along the direction extending from the front to the back vanishes, the sensor device 10 and bracket 22 are returned to their original positions owing to the compression coil spring 31a.

Since the compression coil spring 31a and bolt 31b are provided on the back face of the sensor device 10 at locations corresponding to the four corners of a rectangle, as mentioned above, the sensor device 10 is tiltable up and down as well as to the left and right with respect to the bracket 22. The directions in which the sensor device 10 is tiltable are indicated by the double-ended arrows in FIGS. 2 and 3. Since the sensor device 10 is tiltable, when the sensor face of the sensor device 10 is pressed against the wire rope 2, the sensor device 10 tilts, even if the sensor face is pressed against the wire rope 2 obliquely, and the wire rope 2 is thus easily brought into line contact with the sensor face.

With reference to FIGS. 2 and 3, four tilt regulating screws 32 are screwed into the bracket 22 near respective ones of the above-mentioned four bolts 31b with their distal ends directed toward the back face of the sensor device 10. By turning the tilt regulating screws 32, the amount of protrusion of the tilt regulating screws 32 from the bracket is adjusted. If the amount of protrusion of a tilt regulating screw 32 from the bracket 22 is enlarged, the back face of the sensor device 10 will contact the distal end of the tilt regulating screw 32 when the sensor device tilts. The inclination of the sensor device 10, therefore, can be stopped at this point (no further inclination is allowed). The angle through which the sensor device 10 is capable of tilting is thus adjusted using the tilt regulating screws 32. Naturally, it can also be arranged so that the sensor device 10 is incapable of tilting.

The upper end of the above-mentioned bracket 22 is bent approximately at a right angle and extends horizontally in a direction away from the back face of the sensor device 10. Secured to the horizontally extending end portion of the bracket 22 is the planar bracket 21, which is a substantially equilateral triangle when viewed from the plane. The triangular bracket 21 is secured to the bracket 22 at two of its three vertices, and the end of the columnar handle 23 is secured to the bracket 21 at its one remaining vertex. The handle 23 extends downward.

One side face of the sensor device 10 is provided with an output terminal 18 electrically connected to a signal cable 19 (see FIG. 1). As will be described later, a test signal from the sensor device 10 is transmitted to a control unit through the output terminal 18 and signal cable 19.

Secured to both side faces of the sensor device 10 are positioning fittings 17 having a triangular shape when viewed from the front, each having a centrally provided pin-insertion hole 17a. The details of the positioning fittings 17 will be described later.

Figure 4:
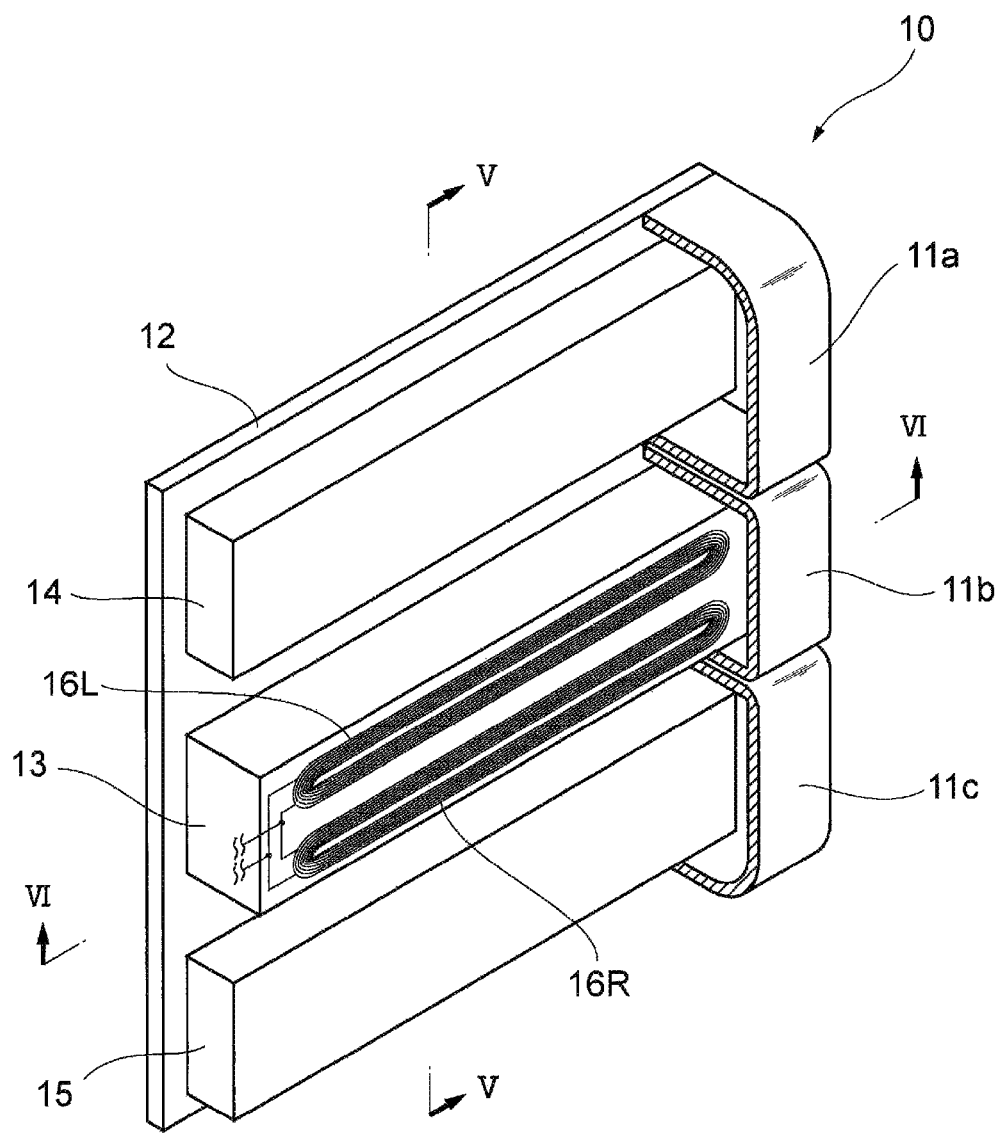
FIG. 4 illustrates the internal structure of a portable rope tester.
Figure 5:
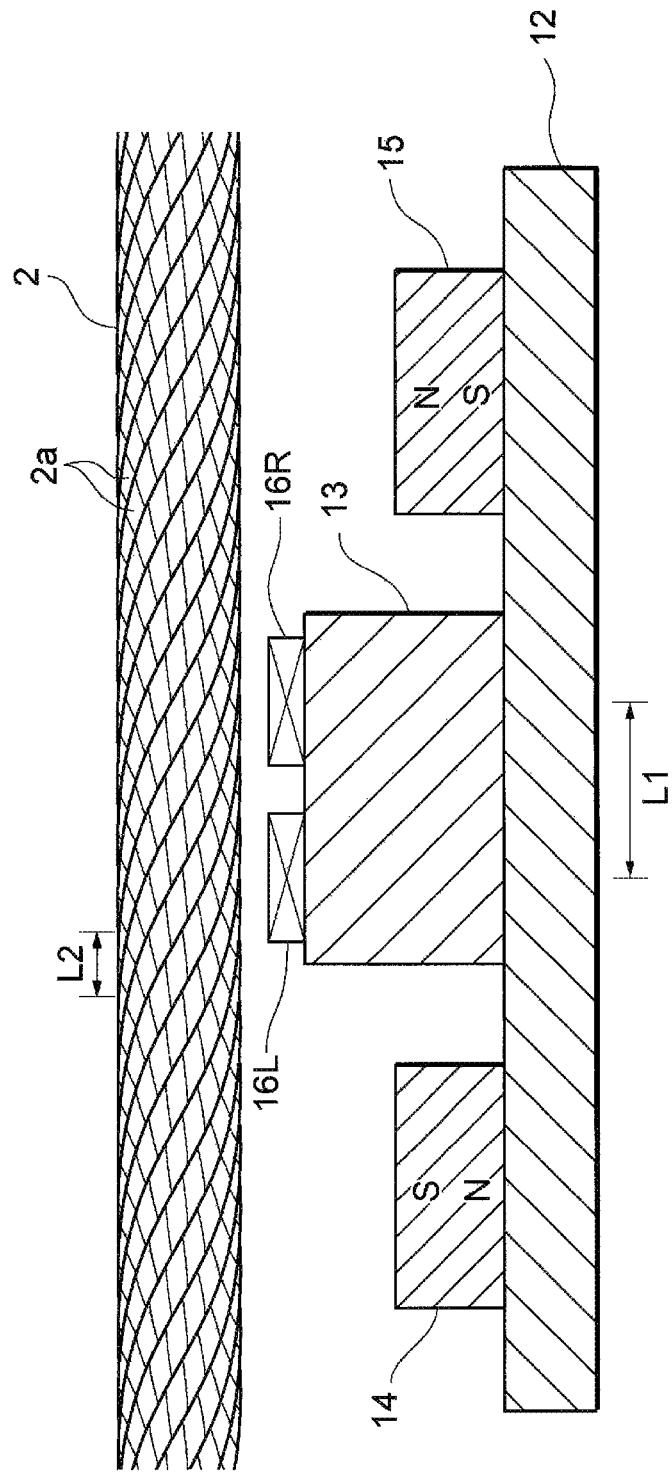
FIG. 5 is a sectional view taken along line V-V of FIG. 4.
Figure 6:
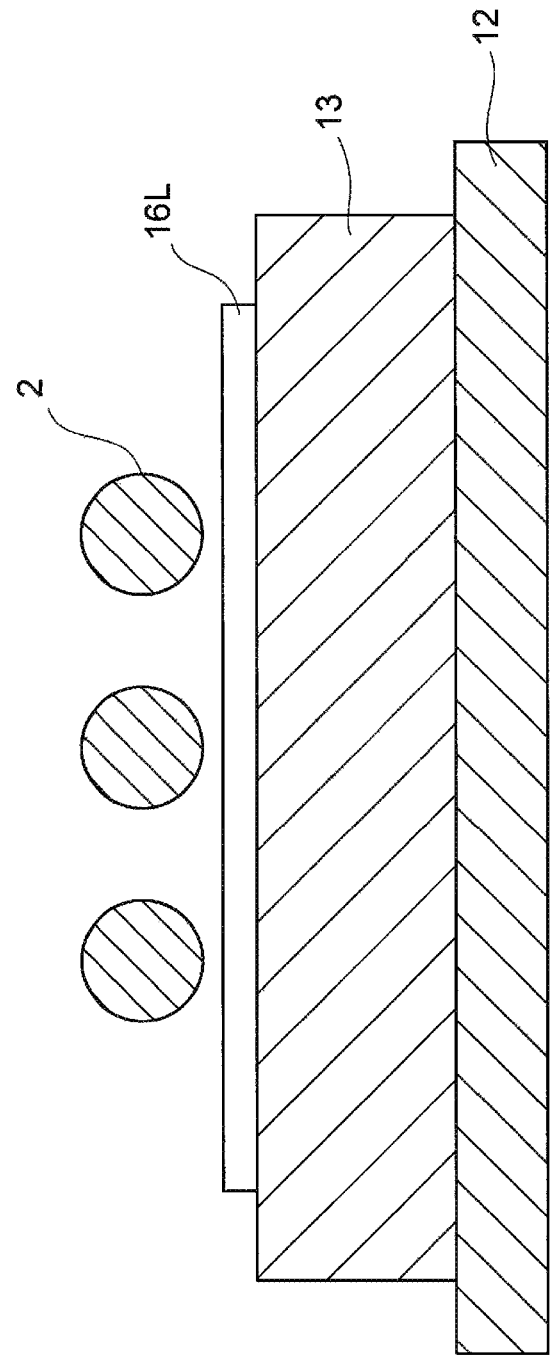
FIG. 6 is a sectional view taken along line VI-VI of FIG. 4.

FIG. 4, which illustrates the internal structure of the sensor device 10, is a perspective view showing, in partially cut-away form, covers that cover the sensor device 10. FIG. 5 shows a sectional view taken along line V-V of FIG. 4 together with wire ropes 2. FIG. 6 shows a sectional view taken along line VI-VI of FIG. 4 together with the wire ropes 2. An illustration of the cover is omitted from FIGS. 5 and 6. Further, the thickness of the members in FIGS. 5 and 6 is shown in exaggerated form in order to facilitate understanding.

The sensor device 10 has a rectangular, flat-plate shaped yoke 12, a pair of magnets 14, 15 secured to both side portions of the yoke 12 in the longitudinal direction thereof, a rectangular parallelepiped-shaped coil base 13 secured to the yoke 12 in spaced relation with respect to the magnets 14, 15, and a pair of planar sensing coils 16L, 16R secured to the top face of the coil base 13. The sensing coils 16L, 16R are thus provided sandwiched between the two magnets 14, 15. The sensing coils 16L, 16R are each obtained by winding a multiplicity of turns of a single fine metal wire. The magnets 14, 15 and sensing coils 16L, 16R all extend longitudinally along the width direction of the sensor device 10 and have a length that extends substantially along the full length of the sensor device 10 in the width direction thereof. With reference to FIG. 4, the magnet 14 is covered and protected by a cover 11a, the coil base 13 and sensing coils 16L, 16R are covered and protected by a cover 11b, and the magnet 15 is covered and protected by a cover 11c. The covers 11a, 11b, 11c are secured to the yoke 12. The flat sensor face of the sensor device 10 is pressed against the wire ropes 2 in such a manner that the longitudinal direction of the magnets 14, 15 and sensing coils 16L, 16R intersects, preferably orthogonally, the longitudinal direction of the wire ropes 2.

With reference to FIG. 5, the magnetic flux generated by the pair of magnets 14, 15 forms a magnetic loop passing through the magnet 15, wire rope 2, magnet 14 and yoke 12, whereby the wire rope 2 is magnetized. Although the wire rope 2 may be magnetized to saturation, it is preferred that magnetization of the wire rope stop at non-saturation. The degree of magnetization of the wire rope 2 can be adjusted depending upon the type of magnets 14, 15, the spacing between the magnets 14, 15 and wire rope 2 and the cross-sectional area of the yoke 12, etc. For example, if ferrite magnets rather than neodymium magnets are used as the magnets 14, 15, the degree of magnetization of the wire rope 2 can be suppressed. Holding magnetization to unsaturated magnetization improves the signal-to-noise ratio (S/N ratio) of the test signal that is output from the sensor device 10. Further, by holding magnetization to unsaturated magnetization, the wire rope 2 and sensor face of the sensor device 10 can be prevented from coming into strong contact owing to magnetic force and it is possible to suppress wear sustained by the wire rope 2 and sensor device 10.

When the magnetized wire rope 2 has damage, magnetic flux leaks from the damaged portion to the exterior of the wire rope 2. Magnetic flux that leaks to the outside of the wire rope 2 shall be referred to as "magnetic leakage flux" below. When the damaged portion of the magnetized wire rope 2 passes by the sensor device 10, electromotive force (emf) is produced in the sensing coils 16L, 16R by this magnetic leakage flux and is represented by a peak in the test signal. Whether or not damage is present in the wire rope 2 and the extent of damage can be detected based upon the peak that appears in the test signal.

Figure 7:
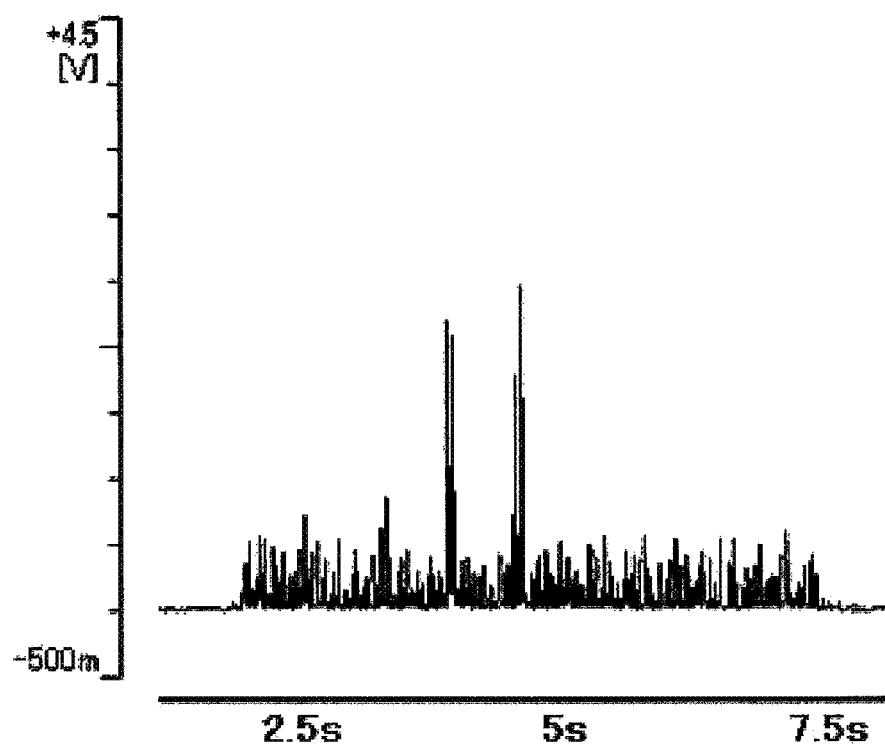
FIG. 7 is a graph representing a test signal.

FIG. 7 is a graph indicating the test signal (after it has undergone signal processing by a control unit, described later) that is output from the sensing coils 16L, 16R. The longitudinal axis is a plot of voltage values. If the wire rope 2 has damage, a peak value (prominent voltage value) appears in the test signal. The greater the amount of magnetic leakage flux, that is, the greater the extent of damage to the wire rope 2, the higher the peak value. The horizontal axis is a time axis. A test signal acquired with the passage of time from left to right along the horizontal axis is indicated.

It will be understood with reference to FIG. 7 that a low-value signal also is being measured constantly. The reason for this is as follows: The wire rope 2 generally is composed of multiple strands 2a twisted together (see FIG. 5), and the surface of the wire rope 2 has unevenness that is formed by the twisting together of these multiple strands. That is, even in the case of a wire rope that is entirely devoid of damage, magnetic leakage flux owing to the unevenness among the strands 2a is present and this appears as the low-value signal in the graph. This waveform that appears owing to unevenness among the strands 2a is referred to generally as strand noise.

In order to minimize strand noise generated owing to unevenness among the strands 2a, the two sensing coils 16L, 16R are differentially connected. This results in cancellation of the signals produced owing to passage through the two sensing coils 16L, 16R of the magnetic leakage flux ascribable to the unevenness among the strands 2a. This makes it possible to suppress strand noise that appears in the test signal. It will suffice if the distance L1 between the two sensing coils 16L, 16R (the spacing between the portions through which the magnetic flux of the two sensing coils 16L, 16R passes) is made an integral multiple of spacing L2 between the crests (peaks) of adjacent strands. The effect of cancellation of strand noise by virtue of the differential connection can be enhanced.

Figure 8:
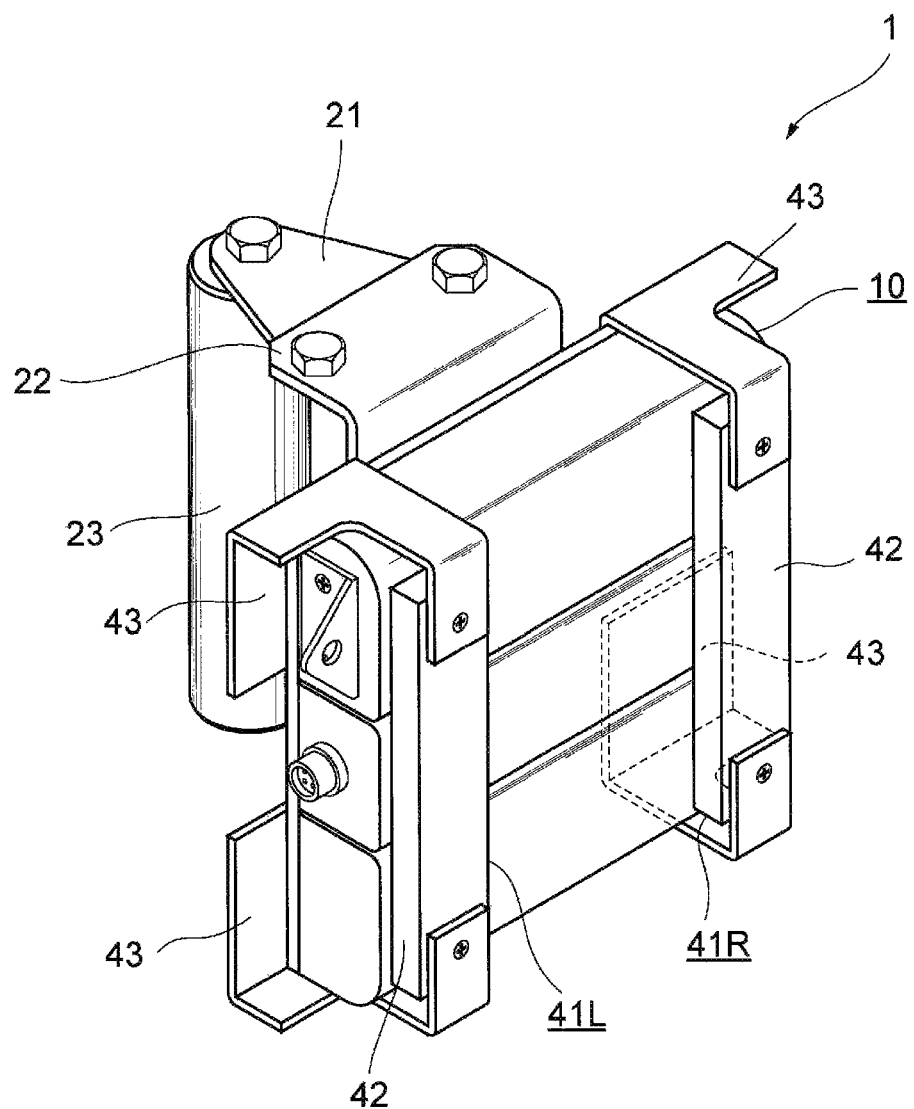
FIG. 8 is a perspective view of a portable rope tester to which guide members have been attached.

FIG. 8 illustrates the rope tester 1 to which guide members 41L, 41R have been attached. The guide members 41L, 41R are used upon being removably fitted onto the sensor device 10 from respective ones of both sides thereof.

Each of the guide members 41L, 41R is constituted by a guide piece 42 in the shape of a rectangular parallelepiped disposed on the sensor face of the sensor device 10 and having a longitudinal direction in the same direction as the longitudinal direction of the wire rope 2 inspected and a prescribed thickness extending outwardly from the sensor face, and a pair of guide pieces 43 secured to respective ones of an upper-end front face and lower-end front face of the guide piece 42, bent at approximately a right angle to extend toward the back face of the sensor device 10 along upper and lower faces thereof, and further bent at a right angle to extend part of the way along the back surf of the sensor device 10. The guide members 41L, 41R fitted on the sensor device 10 are slidable along the width direction of the sensor device 10. A wire rope 2 inspected is sandwiched from both sides by the pair of guide pieces 42. Since movement of a wire rope 2 to the left and right is restricted, a stable inspection signal can be acquired.

In a case where multiple wire ropes 2 are inspected collectively (see FIG. 1), the two wire ropes situated on both sides of the multiple wire ropes are sandwiched by the pair of guide pieces 42.

Figure 9:
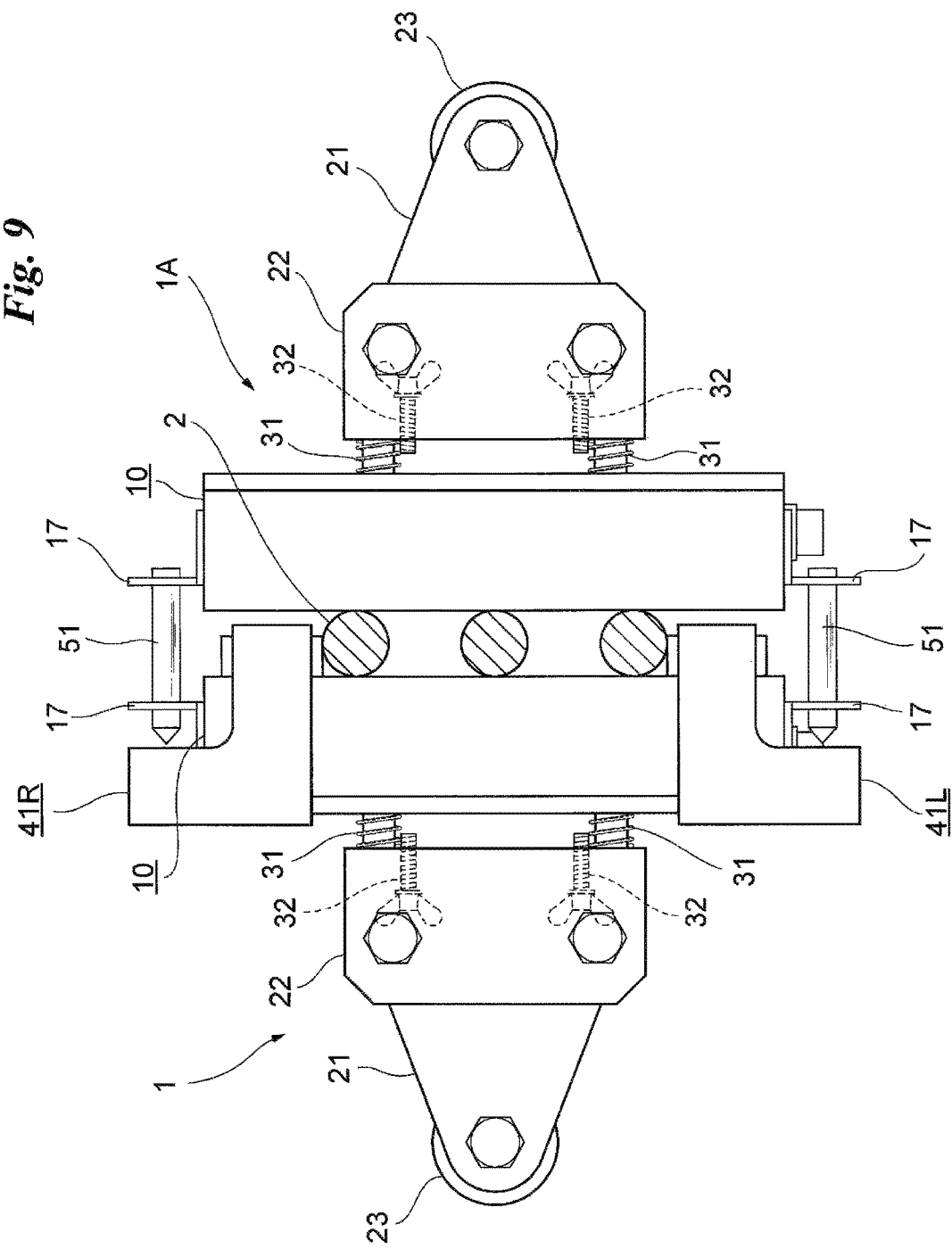
FIG. 9 is a plan view illustrating the manner in which two portable rope testers have been made to oppose each other across wire ropes.
Figure 10:
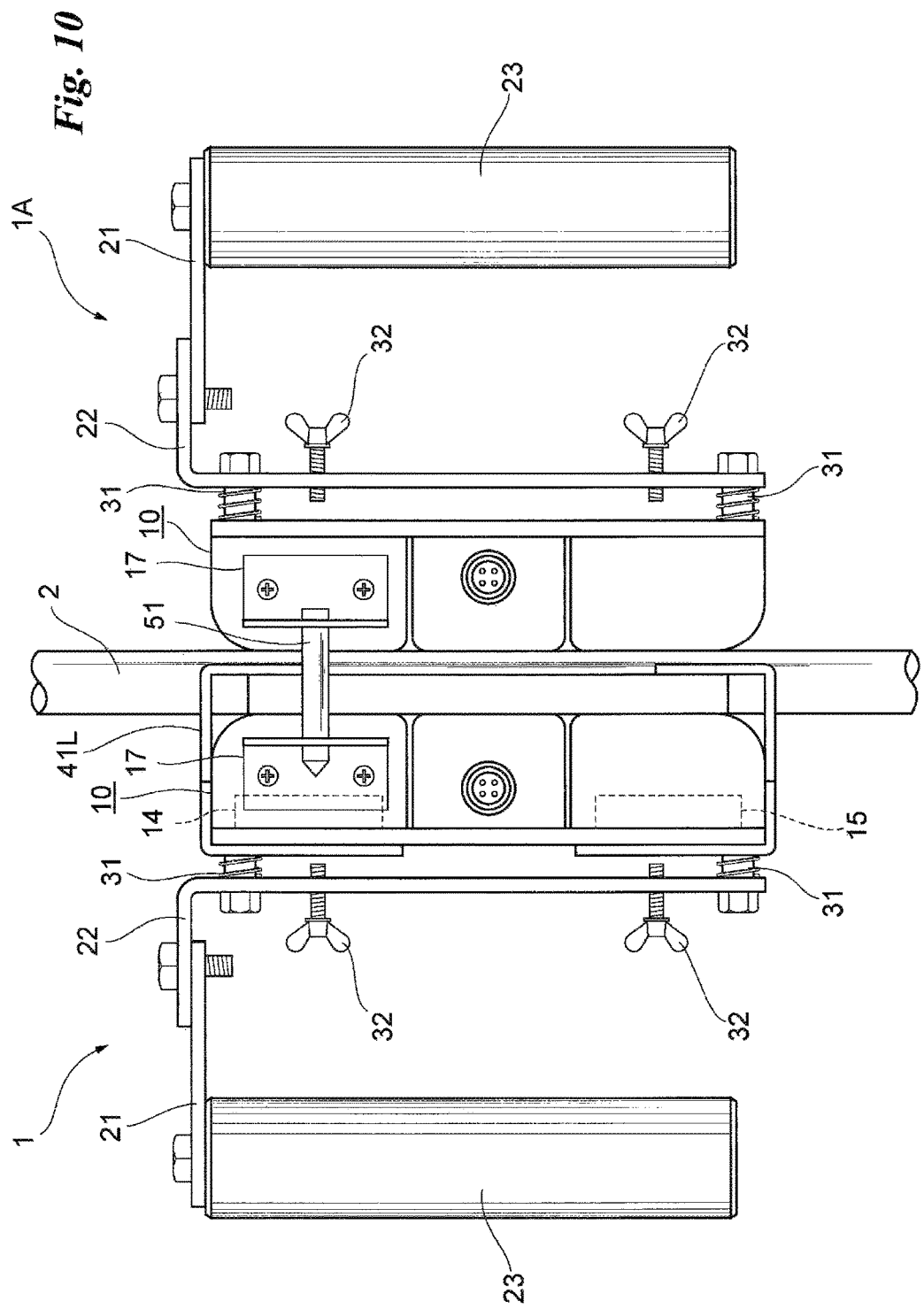
FIG. 10 is a side view illustrating the manner in which two portable rope testers have been made to oppose each other across wire ropes.

FIGS. 9 and 10 illustrate the manner in which wire ropes 2 are inspected from both sides thereof by two portable rope testers. Of the two portable rope testers 1, 1A, the above-mentioned guide members 41L, 41R (see FIG. 8) are fitted onto one rope tester 1 (the one on the left side in FIGS. 9 and 10). Since magnetic leakage flux can be sensed on both sides (both faces) of the wire rope 2 rather than on one side (one face), the accuracy with which damage to the wire ropes 2 is detected is improved.

When the wire rope 2 is inspected from both its sides using the two rope testers 1, 1A, use is made of the above-mentioned positioning fittings 17 that have been secured to both side faces of the sensor device 10. The sensor faces of the sensor devices 10 of respective ones of the two rope testers 1, 1A are made to oppose each other to thereby sandwich the wire rope 2 from both sides, and a positioning pin (connecting pin) 51 is inserted into the pin-insertion hole 17a (see FIG. 1) formed in the center of each positioning fitting 17. The sensor faces of the two rope testers 1, 1A can be made to face each other squarely. The two detection coils 16L, 16R possessed by the sensor device 10 of the rope tester 1 and the two detection coils 16L, 16R possessed by the sensor device 10 of the rope tester 1A can be made to face each other squarely in substantially accurate fashion. Test signals from the same portion of the wire rope 2 along the longitudinal direction thereof can be output from respective ones of the two sensor devices 10 simultaneously. The positioning pin 51 may be secured beforehand to the positioning fitting 17 possessed by one of the two rope testers 1, 1A, e.g., the rope tester 1A.

The sensor devices 10 possessed by the two rope testers 1, 1A may both have the magnets 14, 15 for magnetizing the wire rope 2, and with regard to one of the two rope testers 1, 1A, e.g., the rope tester 1A, the sensor device 10 need not be provided with the magnets 14, 15. If the magnetic force of the magnets 14, 15 possessed by the sensor device 10 of the one rope tester 1 is adequate, the sensor device 10 of the other rope tester 1A is not provided with the magnets 14, 15. In a case where it is desired to provide additional magnetic force, it will suffice if the sensor device 10 of the other rope tester 1A is provided with the magnets 14, 15. If the two rope testers 1, 1A are thus used, adjustment of magnetic force can be performed as well. In a case where both of the sensor devices 10 of the two rope testers 1, 1A are provided with the magnets 14, 15, different sizes and types can be adopted for the magnets 14, 15 possessed by the sensor device 10 of one rope tester 1 and for the magnets 14, 15 possessed by the sensor device 10 of the other rope tester 1A. It goes without saying that the sensing coils 16L, 16R are provided on both of the sensor devices 10 of the two rope testers 1, 1A.

In a case where the two rope testers 1, 1A are used, the test signals that are output from the two sensor devices 10 are superimposed on the signal cable 19 and sent to the control unit.

Figure 11:
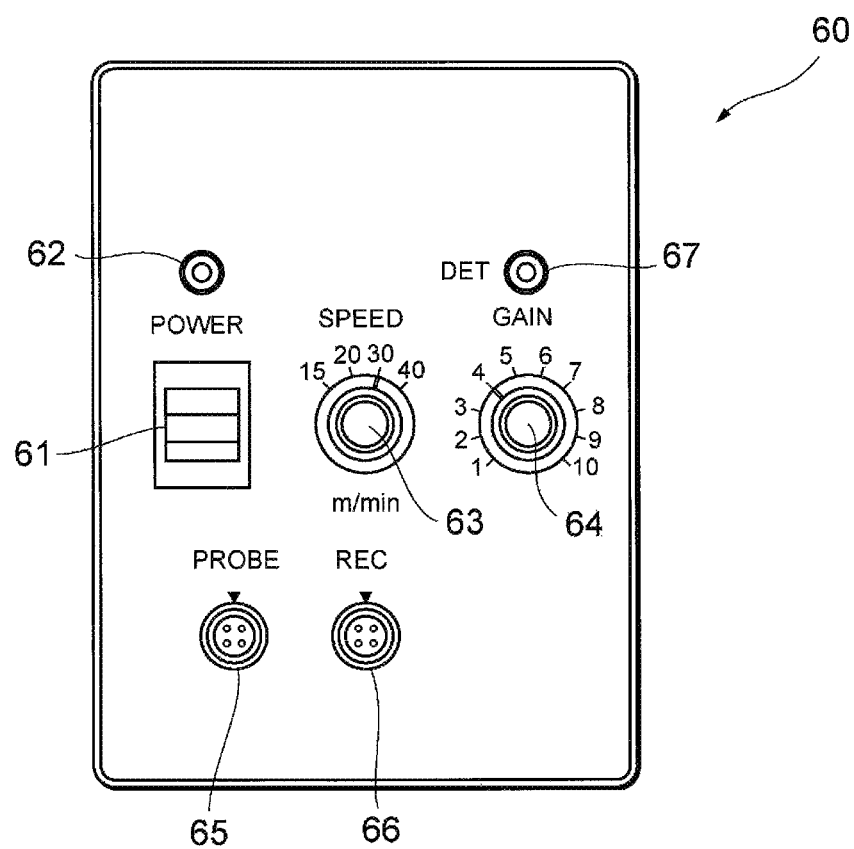
FIG. 11 is a front view of a control unit.
Figure 12:
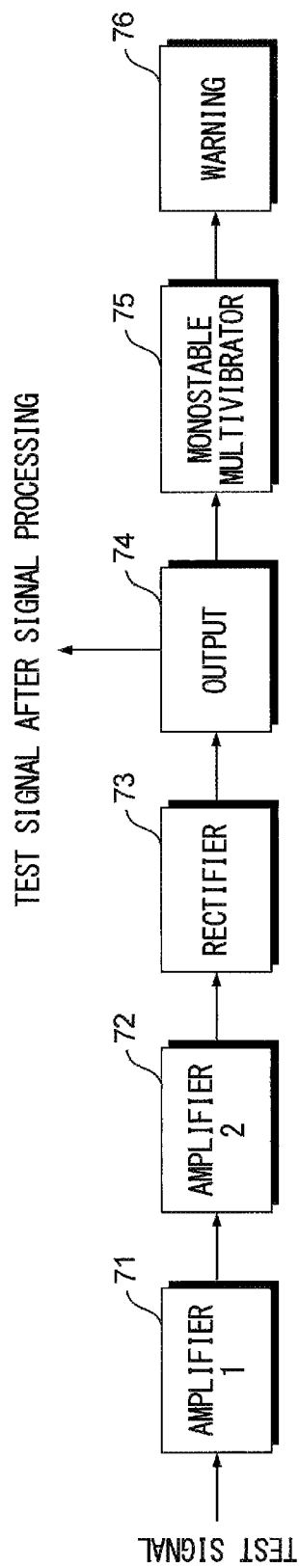
FIG. 12 is a block diagram illustrating the electrical configuration of a control unit.

FIG. 11 illustrates the external appearance of a control unit 60 for processing the test signal that is output from the sensor device 10. FIG. 12 is a block diagram illustrating the electrical configuration of the control unit 60.

The control unit 60 is a unit for applying signal processing to the test signal that is output from the sensor device 10 of the portable rope tester 1 and generating a warning when damage to the wire rope 2 has occurred. The control unit 60 is portable as well, comparatively light in weight and can be carried.

With reference to FIG. 11, the control unit 60 has a power switch 61 for turning a power supply on and off; a power lamp 62 that lights when the power supply is turned on; a speed gain adjustment dial 63 for adjusting gain in accordance with traveling speed of the wire rope 2 (or sensor device 10); a gain adjustment dial 64 for adjusting gain; an input terminal 65, which is for inputting the test signal that has been output from the sensor device 10 and to which is connected one end of the signal cable 19 (see FIG. 1) the other end of which is connected to the output terminal 18 of the sensor device 10; an output terminal 66 for outputting the test signal that has been signal-processed by the control unit 60; a detection lamp 67 that lights when damage to the wire rope is detected; and a buzzer (not shown) for issuing a sound when damage to the wire rope is detected. A battery can be used as the power supply of the control unit 60.

With reference to FIG. 12, the test signal that is output from the sensor device 10 undergoes amplification processing by two, first and second, amplifying circuits 71, 72.

The first amplifying circuit 71 is a circuit for applying gain, which has been adjusted by the speed gain adjustment dial 63 in accordance with the traveling speed of the wire rope 2 (or the traveling speed of the sensor device 10), to the test signal. The emf generated in the detection coils 16L, 16R of the sensor device 10 is proportional to change per unit time of the magnetic flux passing through the detection coils 16L, 16R. If there is a change in the traveling speed of the wire rope 2, therefore, the size of the emf will change and the amplitude of the test signal will fluctuate even if damage to the rope is of the same degree. The first amplifying circuit 71 is used to suppress, and preferably to eliminate, this fluctuation of the amplitude of the test signal ascribable to traveling speed of the wire rope 2. In a case where the traveling speed of the wire rope 2 is high, the gain of the first amplifying circuit 71 is lowered. Conversely, if the traveling speed of the wire rope 2 is low, the gain is raised.

The second amplifying circuit 72 is a circuit for applying gain, which has been adjusted by the gain adjustment dial 64, to the test signal. As will be described later, the control unit 60 generates a warning (lights the detection lamp 67 and causes a sound to issue from the buzzer) when it detects a test signal having a voltage value that exceeds a predetermined voltage values (threshold value). The signal level at which the warning should be issued is controlled by adjusting the amplitude of the test signal by the second amplifying circuit 72. In a case where the warning is to be issued even if the degree of damage is light, the gain is raised. Conversely, in a case where it is arranged so that a warning is not issued when the degree of damage is light, the gain is lowered.

Next, the amplified test signal proceeds to a rectifying circuit 73. As mentioned above, the two sensing coils 16L, 16R possessed by the sensor device 10 are differentially connected. As a consequence, the sensing coils 16L, 16R output test signals the signs of which are opposite each other. The rectifying circuit 73 executes processing that reverses the polarity (sign) of the test signal from either one of the sensing coils 16L, 16R.

The test signal that is output from the rectifying circuit 73 is applied to an output circuit 74, where the signal is split into two branches. The signal on one branch is used as the output from the output terminal 66. The signal-processed test signal that is output from the output terminal 66 can be transmitted through a signal cable to a device such as a signal recording device or waveform display device. For example, by applying the test signal from the output terminal 66 to a waveform display device, the waveform of the test signal (see FIG. 7) will be displayed on the waveform display device. The waveform of the test signal can be checked on site.

The signal on the other branch is input to a monostable multivibrator 75.

When a test signal equal to or greater than a predetermined voltage value (threshold value) is input to the monostable multivibrator 75, the latter outputs a pulse having a predetermined duration. Specifically, when a test signal that has a peak value equal to or greater than the predetermined voltage value owing to the existence of damage to the wire rope 2 is input to the monostable multivibrator 75, the latter outputs a pulse.

The pulse that is output from the monostable multivibrator 75 is input to a warning circuit 76. The warning circuit 76 lights the detection lamp 67 and sounds the buzzer in response to input of the pulse. Notification of damage to the wire rope 2 is given by lighting of the detection lamp 67 and sounding of buzzer.

If damage to the wire rope 2 is detected, generally a more detailed test of the wire rope 2 is conducted subsequently. After a detailed inspection, an operation such as replacement of the wire rope 2 is performed as needed.

The portable rope tester 1 described above is suitable for being carried to the site where the wire rope 2 has been laid and for inspecting the wire rope 2 on site. Naturally, the sensor device 10 having the portable rope tester 1 can be used upon being permanently installed in an elevator, for example, as will be described below.

Figure 13:
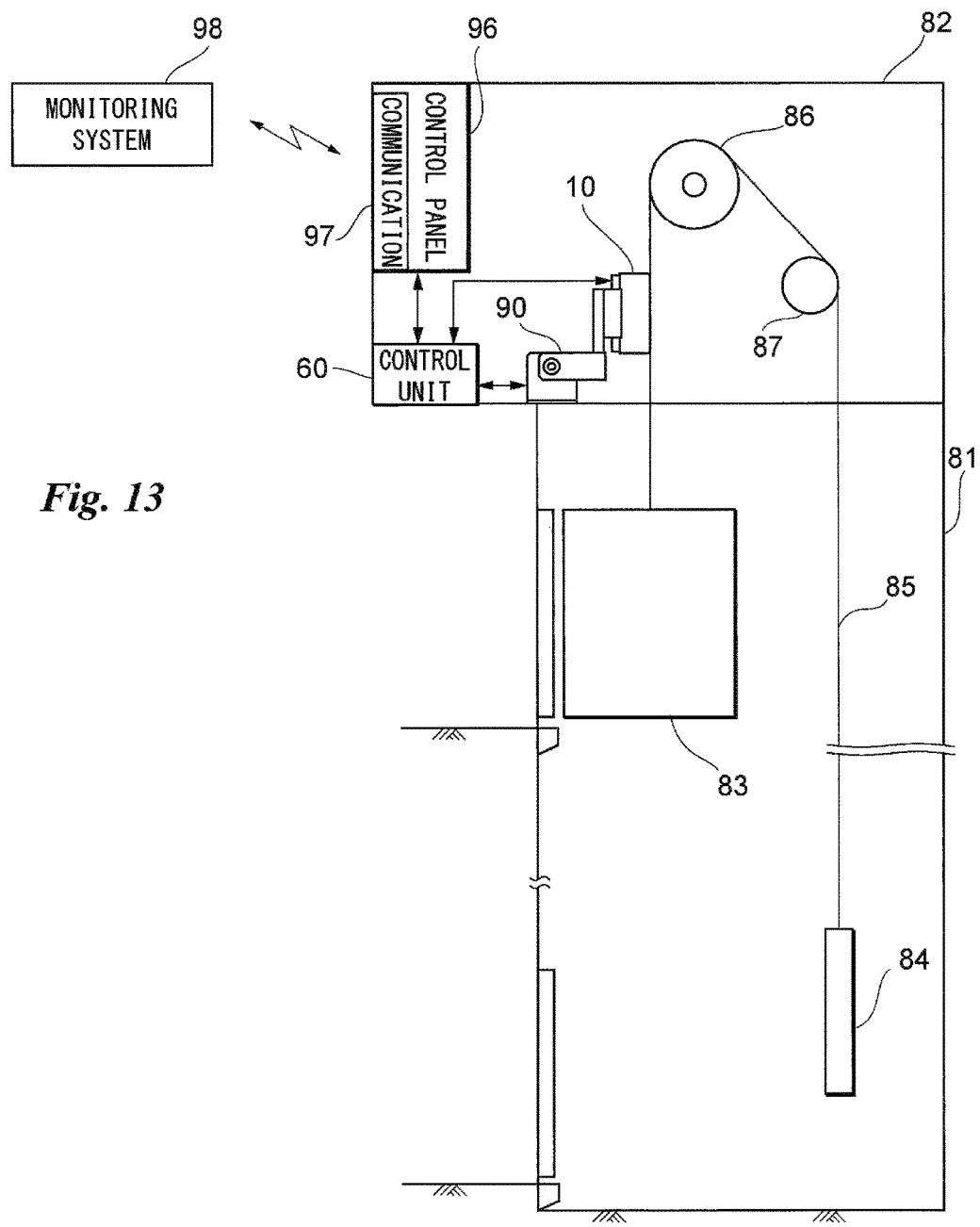
FIG. 13 illustrates the structure of an elevator.

FIG. 13 illustrates the structure of an elevator.

The elevator has a hoistway 81; a machine room 82 provided above the hoistway 81; an elevator car 83 moved up and down inside the hoistway 81 for carrying passengers and cargo; and a wire rope 85 with one end thereof fixed to the upper portion (on the outer side of the ceiling) of the elevator car 83 and the other end thereof fixed to a counterweight 84. In general, multiple wire ropes 85 are used.

The intermediate portion of the wire rope 85 is passed through the interior of the machine room 82, wound upon a hoist 86 provided in the machine room 82 and engaged with a deflector sheave 87. An elevator control panel 96 that includes a communication unit 97 is provided inside the machine room 82. The hoist 86 is controlled by the elevator control panel 96. The wire rope 85 is moved by rotating the hoist 86 forward and backward, whereby the elevator car 83 is raised and lowered inside the hoistway 81.

Further provided inside the machine room 82 are the sensor device 10 for detecting damage to the wire rope 85; a moving mechanism 90 for moving the sensor device 10 in terms of its position; and the control unit 60 for applying signal processing to the test signal that is output from the sensor device 10 and determining the absence or presence of damage to the wire rope 85 and the extent of such damage. The control unit 60 also executes control of the moving mechanism 90, which is described next.

As mentioned above, the elevator control panel 96 provided in the machine room 82 includes the communication unit 97. The communication unit 97 is connected via a network to a monitoring system 98 of an elevator management company. Data indicating the operating status of the elevator is transmitted from the elevator control panel 96 to the monitoring system 98 via the communication unit 97 and the operating status of the elevator is monitored constantly by the monitoring system 98.

The elevator control panel 96 is further connected to the control unit 60 via a signal line. The test signal of the wire rope 85 (or data indicating the presence of damage) is sent from the control unit 60 to the elevator control panel 96, whence the signal is transmitted to the monitoring system 98 of the elevator management system.

Figure 14:
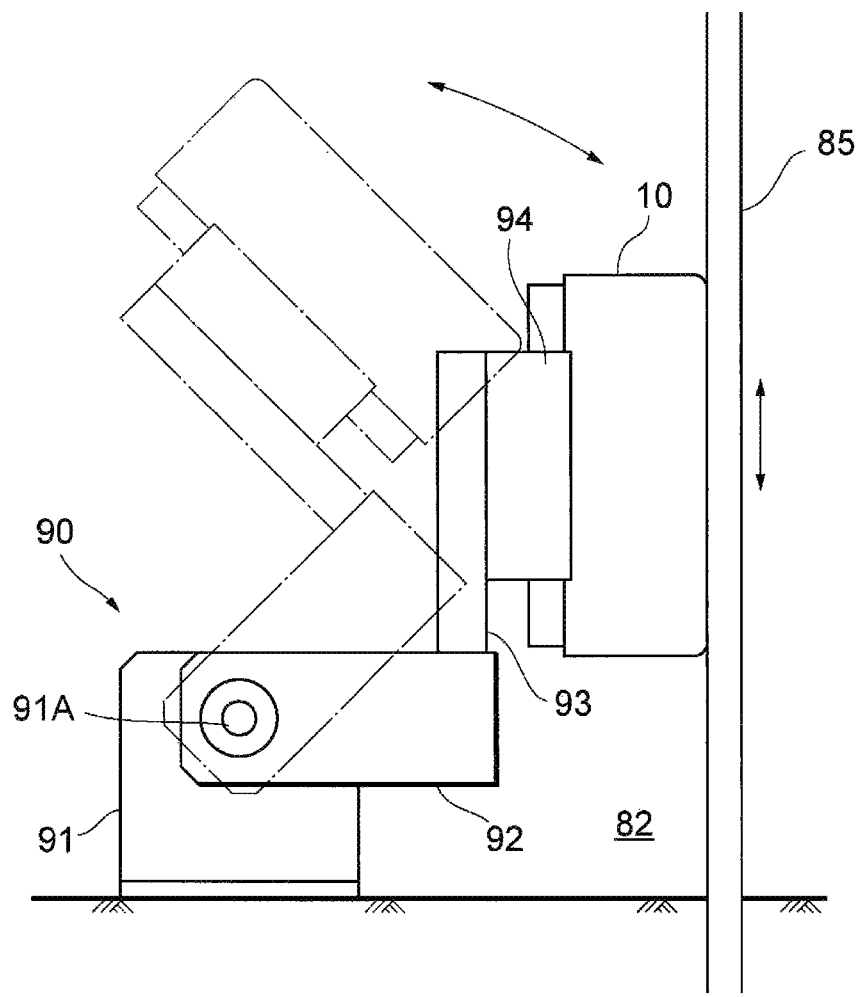
FIG. 14 illustrates the structure of a moving mechanism.

FIG. 14 illustrates the moving mechanism 90, which is provided inside the machine room 82 for moving the sensor device 10 in terms of the position thereof, along with the wire rope 85 when viewed from the side.

The moving mechanism 90 is secured within the machine room 82 and has an induction motor 91 a rotor (not shown) rotated forward and backward through a predetermined angular range. One end of a first arm 92 is secured to a rotary shaft 91A that connects with the rotor of the induction motor 91, and connected to the other end of the first arm 92 is one end of a second arm 93 extending in a direction perpendicular to the longitudinal direction of the first arm 92. A bracket 94 is secured to the other end of the second arm 93, and the sensor device 10 is attached to the bracket 94. The sensor device 10 may be attached to the bracket 94 via a tilting mechanism in such a manner that the sensor device 10 can tilt up and down and to the left and right with respect to the bracket 94, as mentioned above.

When the induction motor 91 is driven, the sensor device 10, describing an arcuate path, moves about the rotary shaft 91A through a predetermined angle.

When inspection of the wire rope 85 by the sensor device 10 is not being carried out, the moving mechanism 90 holds the sensor device 10 in a standby position. The manner in which the sensor device 10 is held in the standby position is indicated by the one-dot chain line in FIG. 14. With the sensor device 10 held in the standby position, the sensor face of the sensor device 10 does not contact the wire rope 85. When a driving voltage is applied to the induction motor 91, the induction motor 91 starts rotating forward (clockwise in FIG. 14). The sensor device 10 gradually approaches the wire rope 85, the flat sensor face of the sensor device 10 is made parallel to the plane defined by multiple wire ropes 85 and is brought into line contact with the wire ropes 85, and here the forward rotation of the induction motor 91 is halted. The position of the sensor device 10 at this time shall be referred to as the "detecting position". The sensor device 10 when at the detecting position is indicated by the solid line in FIG. 14. When the sensor device 10 reaches the detecting position and the sensor face of the sensor device 10 is in line contact with the wire rope 85, inspection of the wire rope 85 is carried out.

One to three times a day, at specific times, for example, the moving mechanism 90 is controlled by the elevator control panel 96 or control unit 60 to move the sensor device 10 from the standby position to the detecting position.

The elevator (car 83) is moved at a speed lower than the usual operating speed, at a speed of 15 meters/second, by way of example, so that the sensor face of the sensor device 10 will pass by the wire rope 85. As described above, the test signal is acquired by the sensor device 10 and an inspection is performed by the control unit 60 to determine whether the wire rope 85 has damage.

When inspection of the wire rope 85 is completed, a driving voltage of the opposite phase is applied to the induction motor 91, whereby the moving mechanism 90 restores the sensor device 10 from the detecting position to the standby position. Since the sensor device 10 moves to the inspecting position only when the wire rope 85 is to be tested, the sensor device 10 and wire rope 85 are not constantly in contact and, consequently, the sensor face of the sensor device 10 and the wire rope 85 sustain little wear.

What is claimed is:

1. A wire rope inspection apparatus having a sensor device for sensing magnetic leakage flux that leaks from a magnetized wire rope, wherein:

said sensor device has a flat sensor face pressed simultaneously against multiple wire ropes arrayed in parallel;
a tilting mechanism is attached to a back side of said sensor device on the side opposite the sensor face;
said tilting mechanism including:
multiple connecting shafts provided projectingly on the back side of said sensor device at respective ones of locations corresponding to four corners of a rectangle at least;
a bracket formed to have through-holes through which respective ones of the multiple connecting shafts pass, said bracket being attached to the back side of said sensor device by the connecting shafts that have been passed through the through-holes;
a fixing member fixed to a distal end portion of each of the connecting shafts passed through the through-holes;
one of a spring or a coil which are provided between said sensor device and said bracket by passing respective ones of the connecting shafts therethourgh, for biasing said sensor device and said bracket away from each other; and
a tilt regulating screw screwed into said bracket movably back and forth near each of the multiple connecting shafts with the distal end of said tilt regulating screw being directed toward a back face of said sensor device;
a single-hand-held handle, which is provided on a back side of said tilt mechanism, being secured to said bracket.

2. A wire rope inspection apparatus according to claim 1, wherein said sensor device has a sensing coil for sensing magnetic leakage flux, and a magnetizer for magnetizing the wire rope.

3. A wire rope inspection apparatus according to claim 2, including first and second sensing coils, these being arranged in parallel, spaced-apart relation and differentially connected;
wherein spacing between portions of respective ones of said first and second sensing coils through which the magnetic leakage flux passes is an integral multiple of distance between adjacent strands of multiple strands that constitute the wire rope.

4. A wire rope inspection apparatus according to claim 1, including first and second sensor devices.

5. A wire rope inspection apparatus according to claim 4, wherein said first sensor device has a sensing coil for sensing magnetic leakage flux, and a magnetizer for magnetizing the wire rope; and
said second sensor device has a sensing coil for sensing magnetic leakage flux and no magnetizer for magnetizing the wire rope.

6. A wire rope inspection apparatus according to claim 4, wherein a positioning fitting having a pin-insertion hole is outwardly projectingly provided on both side faces of each of said first and second sensor devices;
the apparatus further including connecting pins that are passed through the pin-insertion holes for connecting the positioning fittings of said first sensor device to the positioning fittings of said second sensor device.

* * * * *